United States Patent
Zlotnick et al.

(10) Patent No.: US 10,208,358 B2
(45) Date of Patent: Feb. 19, 2019

(54) GENERALIZABLE ASSAY FOR VIRUS CAPSID ASSEMBLY

(71) Applicant: Indiana University Research and Technology Corporation, Indianapolis, IN (US)

(72) Inventors: Adam Zlotnick, Bloomington, IN (US); Stella Vieweger, Louisville, KY (US)

(73) Assignee: Indiana University Reasearch and Technology Corporation, Indianapolis, IN (US)

(*) Notice: Subject to any disclaimer, the term of this patent is extended or adjusted under 35 U.S.C. 154(b) by 0 days.

(21) Appl. No.: 15/304,019

(22) PCT Filed: Apr. 14, 2015

(86) PCT No.: PCT/US2015/025632
§ 371 (c)(1),
(2) Date: Oct. 13, 2016

(87) PCT Pub. No.: WO2015/160726
PCT Pub. Date: Oct. 22, 2015

(65) Prior Publication Data
US 2017/0029907 A1    Feb. 2, 2017

Related U.S. Application Data

(60) Provisional application No. 61/979,213, filed on Apr. 14, 2014.

(51) Int. Cl.
| C12N 7/04 | (2006.01) |
| A61K 39/12 | (2006.01) |
| A61K 39/17 | (2006.01) |
| C12N 7/00 | (2006.01) |
| C12Q 1/68 | (2018.01) |
| C12Q 1/70 | (2006.01) |
| C12Q 1/6818 | (2018.01) |

(52) U.S. Cl.
CPC ........... *C12Q 1/703* (2013.01); *C12Q 1/6818* (2013.01); *C12Q 1/70* (2013.01); *C12Q 2600/136* (2013.01)

(58) Field of Classification Search
CPC ............ G01N 2333/726; C07K 14/005; C07K 14/43595; C07K 2319/60; C12N 15/62
See application file for complete search history.

(56) References Cited

U.S. PATENT DOCUMENTS

| | | | |
|---|---|---|---|
| 6,316,190 B1* | 11/2001 | Rein | A61K 47/48023 424/160.1 |
| 6,593,091 B2* | 7/2003 | Keys | C12Q 1/6818 435/6.11 |
| 2004/0241748 A1* | 12/2004 | Ault-Riche | G01N 33/54353 435/7.1 |
| 2004/0253585 A1* | 12/2004 | Akhavan-Tafti | C12Q 1/485 435/6.14 |
| 2007/0082359 A1* | 4/2007 | Zlotnick | G01N 33/542 435/6.16 |
| 2011/0014706 A2* | 1/2011 | Cao | C07K 14/415 435/419 |
| 2011/0275077 A1 | 11/2011 | James et al. | |
| 2012/0308593 A1* | 12/2012 | Tartaglia | A61K 39/21 424/188.1 |
| 2013/0071849 A1* | 3/2013 | Kong | C07H 19/207 435/6.12 |

OTHER PUBLICATIONS

International Search Report and Written Opinion issued by the ISA/US, Commissioner for Patents, dated Sep. 30, 2015, for International Application No. PCT/US2015/025632; 14 pages.

* cited by examiner

*Primary Examiner* — Barry A Chestnut
(74) *Attorney, Agent, or Firm* — Faegre Baker Daniels LLP

(57) ABSTRACT

Virus capsids protect the viral genome and play roles in its delivery and intracellular transport, making them an attractive target for antiviral therapeutics. The difficulty in targeting capsid assembly is to identify molecules that interfere with the weak protein-protein interactions that drive the reaction. We have developed an in vitro assay for capsid assembly that works on a range of viruses at biologically relevant protein concentrations to facilitate screening large libraries of chemicals for lead compounds.

23 Claims, 7 Drawing Sheets
(7 of 7 Drawing Sheet(s) Filed in Color)
Specification includes a Sequence Listing.

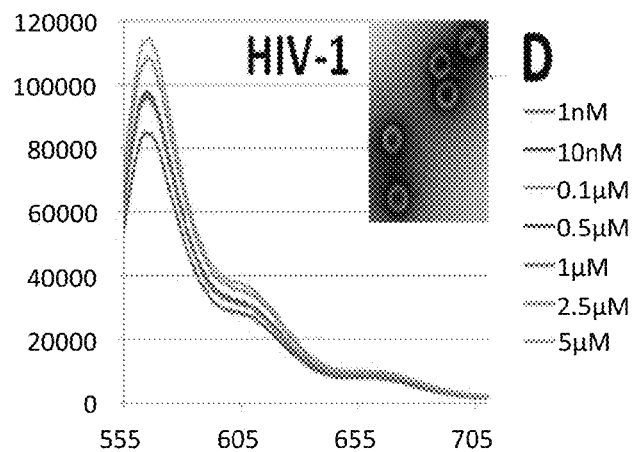
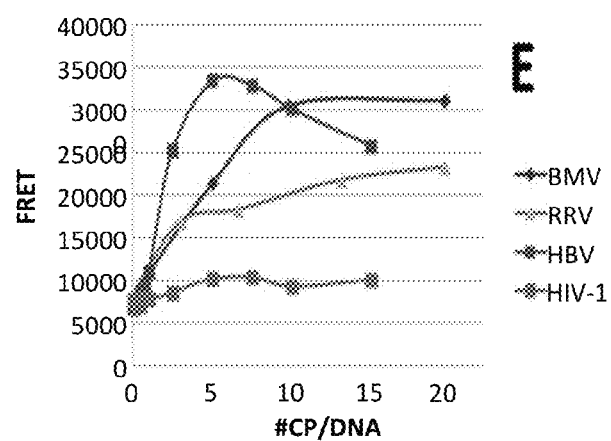
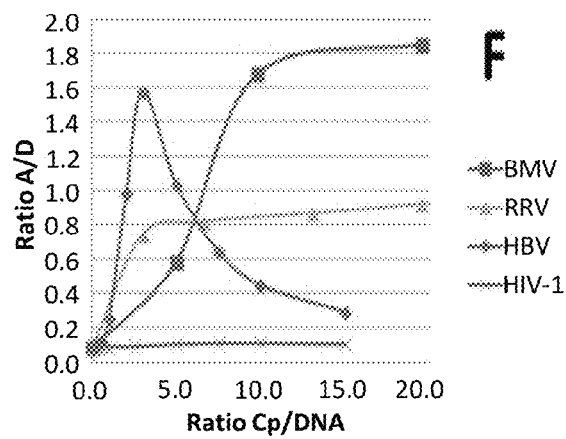
Figure 1 – cont'd

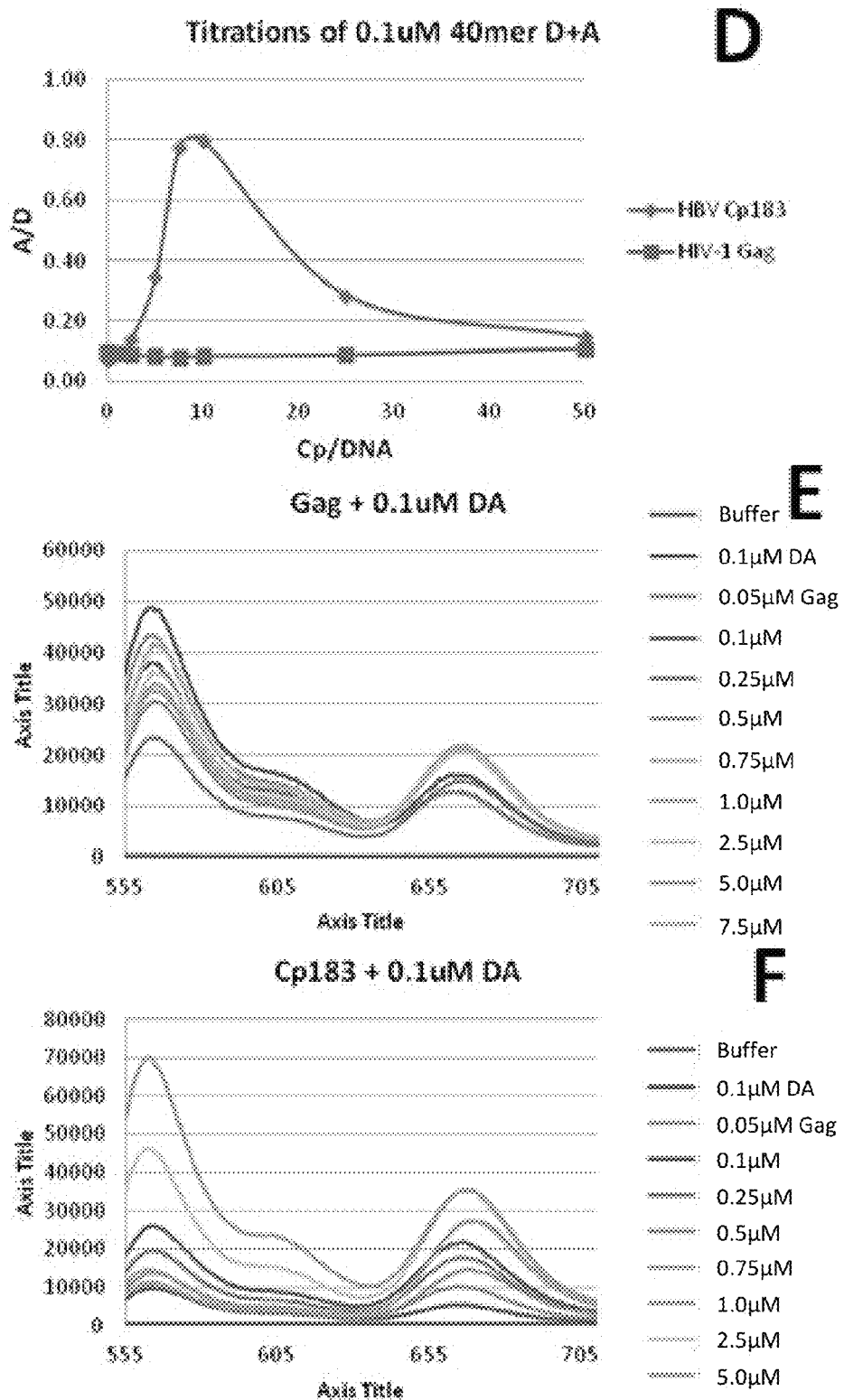
Figure 4 – cont'd

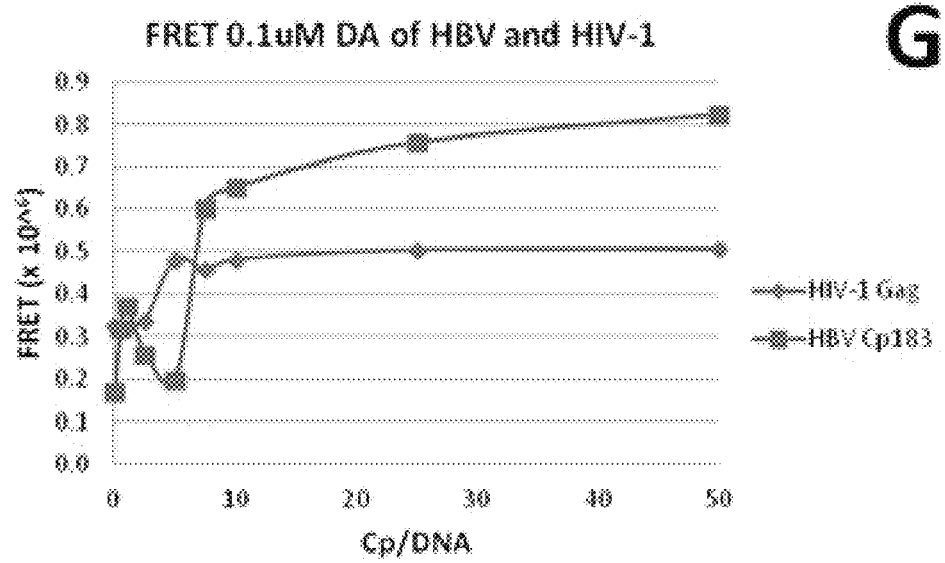
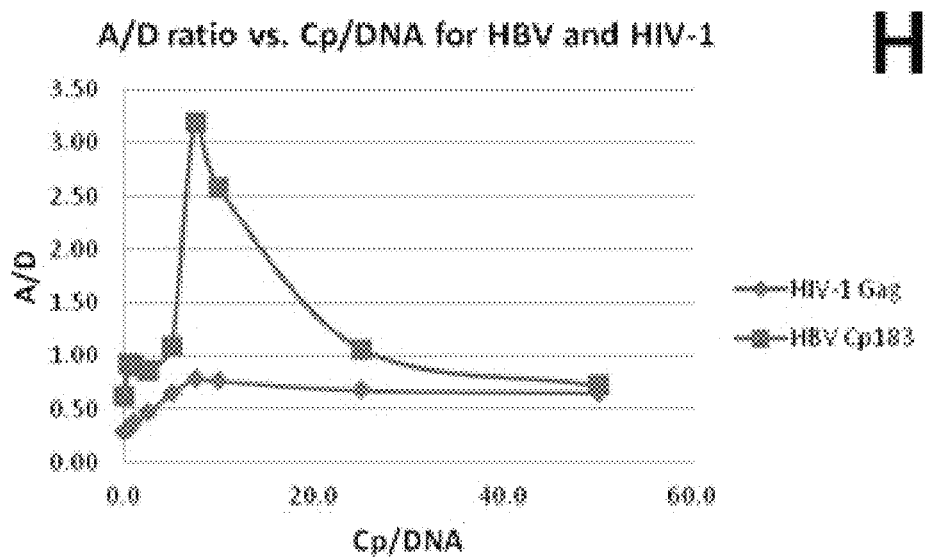
Figure 4 – cont'd

SEQUENCE LISTING

<160> NUMBER OF SEQ ID NOS: 2

<210> SEQ ID NO 1
<211> LENGTH: 40
<212> TYPE: DNA
<213> ORGANISM: artificial sequence
<220> FEATURE:
<223> OTHER INFORMATION: 40 mer for HIV GAG assembly

<400> SEQUENCE: 1
tgtgtgtgtg aaaaaaaaaa aaaaaaaaaa tgtgtgtgtg       40

<210> SEQ ID NO 2

```
<211> LENGTH: 27
<212> TYPE: DNA
<213> ORGANISM: artificial sequence
<220> FEATURE:
<223> OTHER INFORMATION: 27mer for generalized viral assembly

<400> SEQUENCE: 2
tacccacgct ctcgcagtca taattcg                                          27
```

GENERALIZABLE ASSAY FOR VIRUS CAPSID ASSEMBLY

CROSS-REFERENCE TO RELATED APPLICATIONS

This application is a U.S. National Stage Application of International Patent Application No. PCT/2015/025632, filed Apr. 14, 2015, which claims the benefit of U.S. Provisional Patent Application No. 61/979,213, filed Apr. 14, 2014, each of which is incorporated herein by reference in its entirety.

FIELD OF INVENTION

This invention relates to a generalized assay system to analyze assembly effectors in viral assembly. Specifically, the system is used to screen small molecule assembly effectors that prevent viral assembly.

SEQUENCE LISTING

The instant application contains a Sequence Listing which has been submitted via EFS-web and is hereby incorporated by reference in its entirety. The ASCII copy, created on May 21, 2015, is named 20150521_IURTC12097_seq_ST25, and is 690 bytes in size.

BACKGROUND

Viruses comprise a shell or capsid constructed of many copies of one or more relatively small proteins that encase genomic material. In this way viruses show maximum parsimony with their resource (the genome) while taking advantage of their host's resources to manufacture more viruses. A substantial number of viruses package their genomes as they assemble. These include alphaviruses, flaviviruses, retroviruses, hepadnaviruses, some bacteriophages and numerous plant viruses. In some cases the genome may serve as a scaffold that concentrates and organizes protein subunits while in others, it may cross link subunits and induce conformational change. Additionally, the genome may neutralize charges present in nucleic acid-binding domains to overcome electrostatic repulsion between protein subunits.

Assembly reactions must be carefully regulated to proceed successfully. In order for a virus to form, the capsid must assemble on the right nucleic acid and accessory proteins. If the capsid assembles with the wrong geometry, the defects in the resulting virus are likely to render it un-infectious. Similarly, binding the wrong nucleic acid or assembling without nucleic acid will lead to uninfectious virus-like particles. Thus, successful assembly must be triggered in response to a specific signal. Furthermore, in many cases assembly reactions have the ability to "proofread" defects to remove incorrectly positioned proteins. Finally, at the appropriate time capsids must release the genomic material; thus, virus lability is also important to virus lifecycle.

Therefore, virus assembly is a suitable target for antiviral agents, or the so-called Capsid Protein Allosteric Modulators (CpAMs). Drugs that interfere with viral capsid assembly hold potential as CPAM but have proven difficult to identify by conventional screening methods. An easy read out of virus assembly pattern in vitro will bring the benefits of large scale CPAM molecule screening. This disclosure provides a generalized assay system for virus capsid assembly and its use in small molecule assembly effector screening.

SUMMARY

This disclosure provides a generalized in vitro viral assembly assay system. The assay system comprising: a. a physiologically relevant concentration of at least one oligonucleotide that is fluorophore labeled; and b. titrated concentration of viral capsid protein. The fluorophore labeled oligonucleotide could incorporate a fluorescence resonance energy transfer (FRET) donor (D), a FRET acceptor (A), or both (DA). The ratio of D to A is optimized to obtain interpretable energy transfer signal from D to A. For singly labeled oligonucleotides, D and A, the FRET signal in solution is nominal. Assembly of the viral capsid protein concentrates the fluorophore labeled oligonucleotide into resulting viral nucleo-capsid particles and generates D to A FRET signal. For a doubly-labeled oligo, the capsid protein assembly may also bend the oligo to maximize intramolecular FRET.

The disclosure provides a generalized in vitro viral assembly assay system. The system includes a concentration, e.g., a chemically relevant concentration, of at least one oligonucleotide that is fluorophore labeled, wherein said fluorophore is either a donor (D), an acceptor (A), or both (DA), wherein (a) the length of said oligonucleotide, (b) the sequence of said oligonucleotide, and (c) D and A ratio are optimized to obtain energy transfer from D to A; and a concentration of viral capsid protein titrated relative to the concentration of said fluorophore labeled oligonucleotide, wherein said viral capsid protein assembles so that said fluorophore labeled oligonucleotide is associated with the resulting viral nucleocapsid particles and generates a D to A fluorescent signal.

In one embodiment, D is a fluorescence energy resonance transfer (FRET) donor, A is a FRET acceptor, and the fluorescent signal is a FRET signal.

In one embodiment, the assay system further comprises unlabeled oligonucleotides to prevent self-quenching.

In one embodiment, the viral capsid protein is from a self-assembling virus, and said viral capsid protein contains a DNA or RNA binding motif. Self-assembly viruses include (a) members of animal virus families, including togaviridae (e.g. Chikungunya virus, rubella, Venezuelan equine encephalitis), flaviviridae (e.g. Dengue fever, West Nile), hepadnaviridae, astroviridae, birnaviridae, bunyaviridae, caliciviridae (e.g. Norwalk virus), coronaviridae (e.g. SARS), Deltaviridae (HDV), papillomaviridae (e.g. HPV16), paramyxoviridae (e.g Respiratory syncytial virus), polyomaviridae (e.g. BK virus), retroviridae (HIV); and (b) members of plant virus families including bromoviridae, caulimoviridae, dianthoviridae, sobemoviridae, tombusviridae, and tymoviridae. For example, the assay system can include a viral capsid protein from Hepatitis B Virus (HBV), Ross River Virus (RRV), Brome Mosaic Virus (BMV), and Human Immunodeficiency Virus (HIV).

In one embodiment, the assay system includes a fluorophore labeled oligonucleotide comprising between about 5 and about 50 nucleotides. In one embodiment, the fluorophore labeled oligonucleotide D or A has no self-complementary sequence. In one embodiment, the fluorophore labeled oligonucleotide DA comprises 15 to 40 consecutive adenosines. In one embodiment, the fluorophore labeled oligonucleotide is 5'-TGT GTG TGT GAA AAA AAA AAA AAA AAA AAA TGT GTG TGT G-3' (SEQ ID NO: 1) or 5'-TAC CCA CGC TCT CGC AGT CAT AAT TCG-3' (SEQ ID NO: 2).

In one embodiment, the FRET signal is indicative of capsid assembly. In one embodiment, the viral capsid forms a complex that interacts with multiple strands of said labeled oligonucleotide, wherein the viral capsid assembly maximizes the number of labeled nucleotides per capsid, area or unit length; and maximizes intermolecular FRET. In one embodiment, the viral capsid assembly restricts the number of labeled nucleotides per capsid, area or unit length, minimizes intermolecular FRET, and supports intramolecular FRET, wherein a doubly-labeled DA oligonucleotide optionally is used.

The disclosure also relates to a method to screen molecules that target viral assembly. The method includes providing (i) a generalized viral assembly assay system that includes a chemically relevant concentration of at least one oligonucleotide that is fluorophore labeled, wherein said fluorophore is either a donor (D), an acceptor (A), or both (DA), wherein said D and A ratio is optimized to obtain energy transfer from D to A; and (ii) a titrated concentration of viral capsid protein, wherein said viral capsid protein and said fluorophore labeled oligonucleotide partially assemble into a labile complex. The method also includes applying a testing molecule to the viral assembly assay system and measuring a fluorescent signal to ascertain the effect of the testing molecule on assembly.

The disclosure also relates to a method to screen molecules that target alphavirus capsid assembly. The method includes (a) a first fluorophore labeled oligonucleotide, wherein said fluorophore is a donor (D), a second fluorophore labeled oligonucleotide, wherein said second fluorophore is an acceptor (A), and excess unlabeled oligonucleotide; (b) providing an alphavirus capsid protein or a mutant capsid protein at titrated concentration sufficient to allow said capsid protein to assemble on many oligonucleotides to produce maximum fluorescence signal; (c) altering solution conditions to attenuate the association of the capsid protein or the mutant for the nucleotide and produce a reduced fluorescence signal; and (d) providing a testing molecule to said labeled oligonucleotide capsid protein mixture, wherein said molecule reduces or enhances fluorescence signal compared to step c.

In one embodiment, D is a fluorescence energy resonance transfer (FRET) donor, A is a FRET acceptor, and the fluorescent signal is a FRET signal. In one embodiment, the testing molecule is an antiviral agent that may either promote or inhibit capsid assembly. In one embodiment, the solution conditions provide a dynamic range to said testing molecules that may enhance said capsid protein or said mutant capsid protein assembly. In one embodiment, the testing molecule affects the ability of HIV Gag to assemble in the presence of said DA.

The disclosure also relates to a method for screening molecules that target HIV Gag assembly. The method comprises (a) providing a fluorophore labeled oligonucleotide DA, wherein the DA has consecutive adenosines; (b) providing an HIV Gag protein, or a mutant form of Gag protein, at titrated concentration so that an HIV Gag capsid protein or an HIV Gag mutant capsid protein assembles with the fluorophore labeled oligonucleotide DA in a manner of several capsid proteins binding to one oligonucleotide to give maximum fluorescence signal; (c) contriving solution conditions to attenuate the association of the Gag protein or the mutant Gag for the nucleotide and produce a reduced fluorescence signal; and (d) providing a testing molecule to said fluorophore labeled oligonucleotide DA and Gag protein mixture, wherein the molecule reduces or enhances fluorescence signal compared to step c.

In one embodiment, the fluorescence signal is a FRET signal.

In one embodiment, the solution conditions provide a dynamic range to the testing molecules that enhance said Gag protein or said mutant Gag protein assembly. In one embodiment, the testing molecule affects the ability of HIV Gag to assemble in the presence of the fluorophore labeled oligonucleotide DA.

These and other features, aspects and advantages of the present invention will become better understood with reference to the following figures, associated descriptions and claims.

BRIEF DESCRIPTION OF FIGURES

The patent or application file contains at least one drawing executed in color. Copies of this patent or patent application publication with color drawing(s) will be provided by the Office upon request and payment of the necessary fee.

TABLE 1

Figure 1:
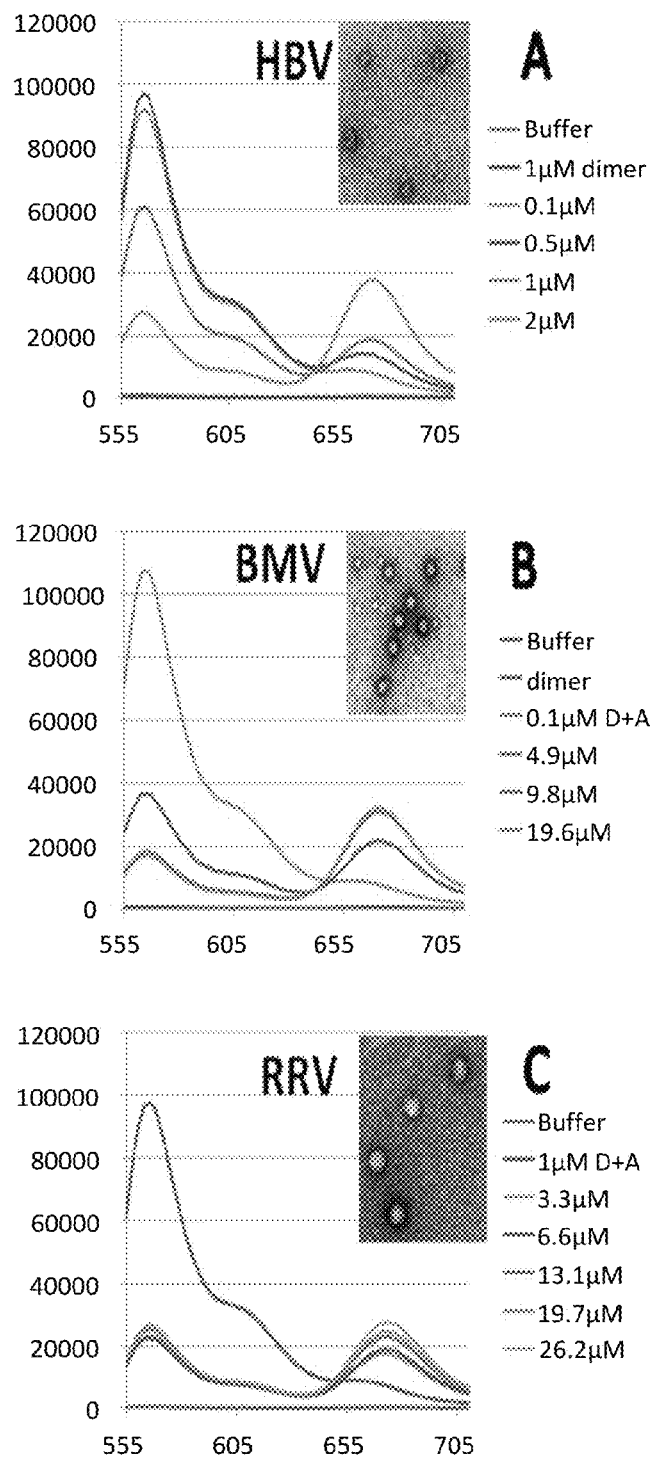
FIG. 1. Emission spectra measured from 555-710 nm for 1:1 donor- to acceptor-labeled oligonucleotides titrated with proteins of (A) Hepatitis B virus (HBV) (B) Brome mosaic virus (BMV) (C) Ross River virus (RRV) and (D) Human Immunodeficiency virus type 1 (HIV-1). Insets show transmission electron micrographs of the assembled products under experimental conditions. Total DNA concentration in all cases was 1 µM; donor excitation wavelength was 545 nm. (E) The effect of protein titration on A-D emission at 670 nm (F) A/D normalized titrations of acceptor to donor emission maxima shown as a function of protein-DNA stoichiometry for all four viruses.

Average hexameric spacing and predicted D-A energy transfer efficiencies for the four classes of viruses investigated. Values for BMV and HBV are measured averages (Chimera software), HIV-1 (Wright et al., 2007) and RRV (Mukhopadhyay et al., 2002) were based on reported literature values.

| Virus  | Spacing (Å) | $(R/R_0)^6$ | E (%) |
|--------|-------------|-------------|-------|
| BMV    | 67          | 3.6         | 21.5  |
| HBV    | 80          | 10.6        | 8.6   |
| HIV-1  | 80          | 10.6        | 8.6   |
| RRV    | 93          | 26.1        | 3.7   |

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure. Generally, the procedures for cell culture, infections, molecular biology methods and the like can be found in the art.

Most virus capsids self-assemble, though in many cases self-assembly is facilitated by a substrate, e.g. nucleic acid. In the assembly reaction, the major driving force is protein-protein affinity ($K_A$). In the system described in this disclosure, the nucleic acid can help support assembly by suppressing electrostatic repulsion, driving allosteric structural changes in the capsid protein, or even contributing to short-range protein-protein interactions; however it is too short to support long range interactions. In this disclosure we provide a capsid protein assembly assay to measure the affinity of protein for protein. In particular, we use this assay to screen small molecules for their ability to affect assembly, which is an antiviral activity.

In screening a library of small molecules, one approach is to choose solution conditions so that there is approximately 50% assembly with enough unbound protein to allow 100% assembly. In this case, a molecule that enhanced $K_A$ would provoke further assembly and an increased FRET signal. Conversely, an assembly inhibitor that decreased $K_A$ would reduce the FRET signal. Because there are advantages to biasing the search to look for assembly-enhancing molecules, solution conditions are generally chosen so that there is about 25% assembly.

To adjust assembly conditions, we modulate electrostatic protein-nucleic acid interactions by adjusting ionic strength—high salt will weaken binding of protein to nucleic acid and thus nucleic acid-induced assembly. Another approach is to modify the oligonucleotide. A shorter or longer oligo tends to modify affinity—usually a longer length enhances binding {Tellinghuisen, 1999 #2012}. A sequence rich in adenosine tends to favor rigidity of the oligonucleotide while enrichment in thymine favors flexibility {Sanger, 1988 #6070}. Yet another approach is to modulate protein-protein interactions. Many such interactions are sensitive to pH or chaotropes, for example, e.g. guanidinium HCl or urea can be used to modify assembly conditions to weaken protein-protein association.

Spherical viruses have a shell or capsid constructed of many copies of relatively small proteins; these encase the viral genome. In this way viruses show maximum parsimony with their resource (the genome) while taking full advantage of their host's resources to manufacture more viruses. A substantial number of viruses package their genomes as they assemble. These include alphaviruses, retroviruses, hepadnaviruses, some bacteriophages and numerous plant viruses. The genome may serve as a scaffold that helps to concentrate and organizes protein subunits. The genome may neutralize charges present in nucleic acid-binding domains to overcome electrostatic repulsion between protein subunits. At least in the case of HIV Gag, binding of nucleic acid also appears to induce proteins to become assembly competent.

In this disclosure we used short oligonucleotides to induce assembly while minimizing nucleic acids' long range effects. This provides an avenue to investigate the driving forces of assembly. We developed a tool for observing nucleic acid binding to protein subunits among four distinctly different viruses: Hepatitis B Virus (HBV)—a hepadnavirus, Ross River Virus (RRV)—an alphavirus, Brome Mosaic Virus (BMV)—a plant virus, and Human Immunodeficiency Virus Type 1 (HIV-1)—a retrovirus.

Three of these viruses are icosahedral, that is, they have a geometrically regular capsid composed of pentameric and hexameric vertices. BMV is a T=3 icosahedral non-enveloped virus comprising 90 homodimers and a positive strand RNA genome. The capsid protein subunits are characterized by a flexible N-terminal RNA binding domain attached to a beta-barrel core. In vitro assembly at neutral pH and moderate ionic strength occurs only in the presence of RNA via electrostatic interactions with the genome. Empty capsids do not assemble under these conditions. BMV and closely related Cowpea Chlorotic Mottle Virus subunits can be induced to assemble into smaller particles of 60 and 30 dimers.

RRV is an enveloped RNA virion also with a T=4 nucleocapsid core. In vivo, nucleocapsid core formation precedes glycoprotein association with membrane and subsequent budding. In vitro, core formation requires nucleic acid; cores form in the presence of ssDNA but not dsDNA. Short oligonucleotides can modulate assembly such that capsid stability and morphology is modulated by the length of the DNA {Tellinghuisen, 1999 #2012}.

HBV is an enveloped DNA virus whose T=4 icosahedral core formed by 120 copies of the homodimeric, 183 residue core protein (Cp183). Cores initially assemble on an ssRNA that is reverse transcribed in the core's interior. The nucleic acid binding domain of HBV Cp183 amino acids is comprised of residues 150-183. Unlike BMV and RRV capsid proteins, HBV core protein self-associates at near physiological conditions with or without nucleic acid.

Unlike the capsids of BMV, RRV, and HBV, retrovirus cores are not icosahedral, though HIV-1 Gag forms paracrystalline lattices with some hexameric order. In vivo, HIV-1 assembles on the plasma membrane from thousands of copies of its Gag polyprotein; some retroviruses assemble in the cytoplasm. Lateral interactions between Gag molecules are mediated by its capsid (CA) and peptide spacer (SP1) domains. Association with nucleic acid (by the NC domain) is believed to support Gag dimerization and allosterically trigger retrovirus assembly. For our in vitro assembly studies, we used a mutant of the HIV-1 Gag polyprotein (GagΔ) lacking most of the N-terminal matrix domain and the C-terminal p6 domain; GagΔ assembles in a nucleic acid dependent manner into particles that resemble immature capsids in structure and size.

To examine the role of protein-protein interactions in nucleic acid driven virus assembly, we have developed a FRET-based assay using short oligonucleotides with either a donor (D) or an acceptor (A) fluorophore covalently bound at the 5'-end, or with both 5'-donor and 3'-acceptor (DA). The fact that only the DNA was labeled in these experiments makes this assay generalizable across different classes of proteins without labeling the protein. In this disclosure, we have shown that viruses organize their nucleic acid in distinctly different geometries and in a protein concentration dependent manner. In particular, our data indicate that HIV-1 Gag assembly is driven by binding a single DNA oligomer per vertex, unlike the other viruses which are less restrictive. This result suggests that the way Gag organizes nucleic acid during assembly is critical to HIV biology.

Although a FRET-based detection system was used in certain embodiments described herein, the skilled artisan recognizes that similar fluorescence-based detection systems known in the art can be used.

Materials and Methods

Oligonucleotides and Proteins

All single strand oligodeoxynucleotides (ssDNAs) were obtained from Integrated DNA Technologies (IDT). Two nucleotide lengths—a 27-mer, 5'-TAC CCA CGC TCT CGC AGT CAT AAT TCG-3' (SEQ ID NO:2), and a 40-mer, 5'-TGT GTG TGT GAA AAA AAA AAA AAA AAA AAA TGT GTG TGT G-3' (SEQ ID NO: 1) were tested, in the present disclosure, but the skilled artisan will appreciate that oligonucleotides of a wide variety of lengths and sequences can be used, as long as they are suitable for binding to the particular capsid protein in accordance with the disclosed systems and assays.

For example, oligonucleotides suitable for use in the disclosed systems and methods can be between about 5 and about 50 nucleotides long. In certain embodiments, the oligonucleotide is between about 5 and about 15 nucleotides, between about 5 and about 20 nucleotides, between about 5 and about 25 nucleotides, between about 5 and about 30 nucleotides, between about 5 and about 35 nucleotides, between about 5 and about 40 nucleotides, between about 5 and about 45 nucleotides, between about 10 and about 20 nucleotides, between about 10 and about 30 nucleotides, between about 10 and about 40 nucleotides, between about 10 and about 50 nucleotides, between about 15 and about 25 nucleotides, between about 15 and about 35 nucleotides, between about 15 and about 45 nucleotides, between about 20 and about 30 nucleotides, between about 20 and about 40 nucleotides, between about 20 and about 50 nucleotides, between about 25 and about 35 nucleotides, between about 25 and 45 nucleotides, between about 30 and about 40 nucleotides, between about 30 and about 40 nucleotides, between about 35 and about 45 nucleotides, and between about 40 and about 50 nucleotides.

The modifications made to these oligonucleotides included a donor (D) at the 5'-end, an acceptor (A) at the 5'-end, and in the case of the 40-mer only, a donor (D) at the 5'-end and an acceptor (A) at the 3'-end of the same strand.

All virus capsid proteins were expressed and purified according to published protocols—BMV (Gopinath 2005, Marillonnet 2005, Willy 1997), HBV (Porterfield 2010), RRV (Cheng 2011, Tellinghuisen 1999) and HIV-1 Gag (Datta 2009). RRV and BMV proteins were generously provided by the Mukhopadhyay and Dragnea laboratories at Indiana University respectively. For in vitro studies of HIV-1, Gag polyprotein in which both the p6 domain and the membrane binding segment of the MA domain are deleted was used (Campbell 2001; Gross 2000). This Gag variant is referred to as GagΔ.

Purified samples of nucleic acid and protein were characterized by UV-VIS absorption. DNA concentrations were determined at 260 nm with extinction coefficients provided by IDT. Extinction coefficients used in determining protein concentrations were estimated from amino acid content to be 30400 $M^{-1}$ $cm^{-1}$, 39670 $M^{-1}$ $cm^{-1}$, 23950 $M^{-1}$ $cm^{-1}$ and 47940 $M^{-1}$ $cm^{-1}$ for HBV, RRV, BMV and GagΔ proteins respectively.

Assembly Reactions

Assembly reactions were set up as titrations of a given concentration of nucleic acid. Assembly was initiated by mixing nucleic acid with capsid protein in assembly buffers appropriate to the virus and incubating as needed—50 mM Tris pH 7.5 for HBV; 50 mM Tris pH 7.4, 50 mM NaCl, 10 mM KCl, 5 mM $MgCl_2$ for BMV; 20 mM HEPES pH 7.5, 0.15 M NaCl, 0.1 mM EDTA for RRV; 20 mM Tris pH 8, 1 mM DTT for HIV-1 GagΔ.

Assembly was monitored by fluorescence. All reactions were carried out at 21° C. For the Cy3 donor and Cy5 acceptor fluorophores, fluorescence emission spectra for FRET experiments was measured from 555-710 nm. For measuring FRET in titrations, donor and acceptor excitation wavelengths were 545 and 645 nm respectively. Acceptor emission was measured at 670 nm.

Dynamic light scattering and stained electron microscopy were used to further characterize assembly products. Samples for electron microscopy were prepared on 300 mesh carbon-coated copper mesh grids and stained with 2% uranyl acetate.

The following examples use FRET based assay to analyze various families of viral assembly, and prophetic use of this FRET based assay to screen small molecules that target viral assembly.

Example 1. Intermolecular FRET

Capsid protein assembly is often induced by nucleic acid by non-covalently crosslinking proteins through their nucleic acid binding domains and by neutralizing repulsive electrostatic charge. By using oligonucleotides labeled with fluorophores we expected to be able to monitor assembly. In FRET, a donor (D)—acceptor (A) pair is chosen such that upon donor excitation, energy is transferred non-radiatively to the acceptor. The efficiency of this energy transfer, E, is dependent on the sixth power of the distance between the D-A pair. The donor and acceptor of choice for these experiments were Cy3 (D) and Cy5 (A) respectively, but any FRET pair known in the art can be used in the disclosed method. The ratio of acceptor to donor emission was used to normalize results from different virus systems. Absence of a FRET signal indicated spacing between donor and acceptor larger than the Forster distance, $R_0$, which was 54 Å for a Cy3-Cy5 FRET pair on oligonucleotides in the absence of protein (Ha, 2002; Sabanayagam, 2005). Fluorophores useful in the systems and methods of the present disclosure include those in Table 2.

TABLE 2

| Fluorochrome | $\varepsilon_{max}$ $M^{-1}cm^{-1}$ | Absorbance max (nm) |
|---|---|---|
| Cy5 | 250,000 | 649 |
| Cy5.5 | 250,000 | 675 |

TABLE 2-continued

| Fluorochrome | $\varepsilon_{max}$ M$^{-1}$cm$^{-1}$ | Absorbance max (nm) |
|---|---|---|
| Cy7 | 250,000 | 743 |
| AlexaFluor660 | 132,000 | 663 |
| AlexaFluor680 | 184,000 | 679 |
| AlexaFluor750 | 280,000 | 749 |
| VivoTag680 (VT680) | 100,000 | 670 |
| VivoTag-S680 | 220,000 | 674 |
| VivoTag-S750 | 100,000 | 750 |
| Dy677 | 180,000 | 673 |
| Dy682 | 140,000 | 690 |
| Dy752 | 270,000 | 748 |
| Dy780 | 170,000 | 782 |
| DyLight547 | 150,000 | 557 |
| DyLight647 | 250,000 | 653 |
| IRDye800CW | 240,000 | 774 |
| IRDye800RS | 200,000 | 767 |
| IRDye700DX | 165,000 | 689 |
| ADS780WS | 170,000 | 782 |
| ADS830WS | 240,000 | 819 |
| ADS832WS | 190,000 | 824 |

In this example, capsid proteins from BMV, RRV, HBV, or HIV-1 titrated a given concentration of oligonucleotide made up of a 1:1 molar ratio of donor-labeled 27-mer ($D_{27}$) and acceptor-labeled 27-mer ($A_{27}$). Given the ratio of D to A present, observed FRET signal in this system would result from the association of protein to two or more labeled ssDNA strands to bring their fluorophores in proximity.

In HBV titrations of A and D labeled 27mers, the increase in FRET signal was accompanied by a change in light scattering and the appearance of capsids by EM (FIG. 1A and inset). This indicated that short (27-mer) ssDNA induced Cp183 assembly into nucleoprotein complexes.

Given our experience with HBV, we chose to optimize the ratio of A:D:unlabeled oligomer with this system. Quenching effects resulting from interactions of protein with the fluorophores or from self-quenching from D-D and A-A interactions were likely. To account for these effects on the observed FRET signal, assay optimization studies were conducted by titrating Cp183 protein with dilutions of labeled oligonucleotides with their unlabeled counterparts. The results from these studies revealed that the chosen molar ratio of 1:1 D to A gave identical FRET signal under the same experimental conditions. Thus, for this protein and the Cy3-Cy5 FRET pair, the optimal ratio appeared to be 1:1:0, i.e. there was no substantive self-quenching with the Cy3-Cy5 FRET pair.

Using the optimized A:D ratio, we evaluated the sensitivity of this FRET assay for assembly. This was necessary to determine if reaction volumes and concentrations could be lowered to physiologically relevant levels. Initial FRET experiments were assayed at 1 µM 27-mer DNA concentrations and progressively lowered for each series of protein titrations. The minimum detectable concentration of DNA in these assays is 50 nM. Initial results shown in FIG. 1 are protein titrations of 1 µM DNA showing the assay works under more aggressive conditions. Assembly led to an increase in FRET, that was maximal at a specific protein concentration and then fell as more protein was added.

BMV led to a monotonic increase in fluorescence (1B, E) and a resulting increase in FRET efficiency (1F). Unlike HBV, the BMV capsid requires oligonucleotides for capsid stability, thus, at high concentrations of BMV capsid protein, the oligos were not diluted over large capsids and the FRET signal did not diminish.

Figure 2:
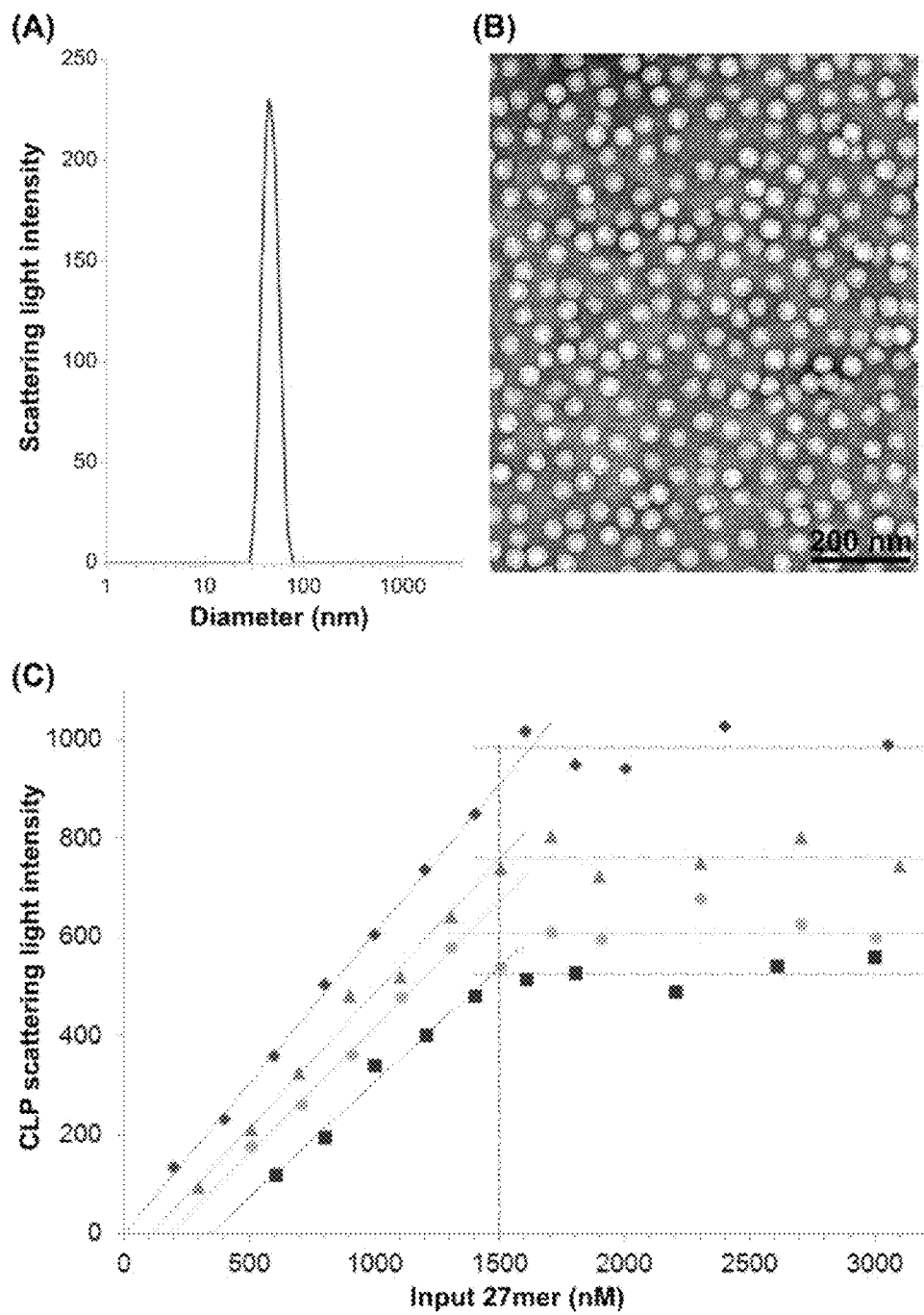
FIG. 2. Titration of alphavirus capsid protein by unlabeled DNA 27mer. Titrations lead to formation of regular capsids based on dynamic light scattering (A) and electron microscopy (B). (C) Titrations at 170 mM (blue), 150 mM (cyan), 110 mM (green) and 50 mM NaCl (red) reveal an ionic strength dependent pseudo-critical concentration, the X-intercept, that is directly proportional to the dissociation constant for subunit-subunit interaction.

In the presence of ssDNA, Ross river virus (RRV) assembles into core-like particles identical to wild type nucleocapsid cores (Tellinghuisen et al., 1999). Titrating labeled DNA oligomers with purified RRV capsid protein of RRV resulted in assembled particles as seen in the inset of FIG. 1C. Assembled particles gave enhanced FRET signal indicating binding to multiple oligonucleotides. RRV displays a rather narrow dynamic range of FRET intensity over a very broad range of protein concentration used (3.3-26.2 µM) compared to BMV and HBV. RRV particle conformation was confirmed by dynamic light scattering, electron microscopy. Titrations and the presence of pseudo-critical concentration of assembly were confirmed by static light scattering (FIG. 2).

Unlike the three other nucleic acid-binding virus capsid proteins, no noticeable change in FRET signal was observed when HIV-1 GagΔ was used to titrate the $D_{27}$-$A_{27}$ mixture (FIG. 1D). Despite the lack of FRET signal in the assay, dynamic light scattering (not shown) and electron micrographs (FIG. 1D inset) showed capsids assembled at protein concentration 5 µM or greater.

A comparison of the titration results for all the viruses provides further insight into the nature of nucleic acid binding in all 4 systems. FIG. 1E shows the signal at 670 nm as a function of protein-DNA stoichiometry, this signal includes both FRET and response to changes in environment. FIG. 1F shows the same data normalized in terms of the A emission over the D emission, proportional to FRET efficiency. BMV and RRV titrations both resemble binding profiles. BMV saturates at about ten proteins per oligo. RRV binding saturates at four proteins per oligonucleotide. The intensity of the RRV signal is lower than that of BMV or HBV, an observation that suggests lower efficiency of energy transfer compared to BMV.

Figure 3:
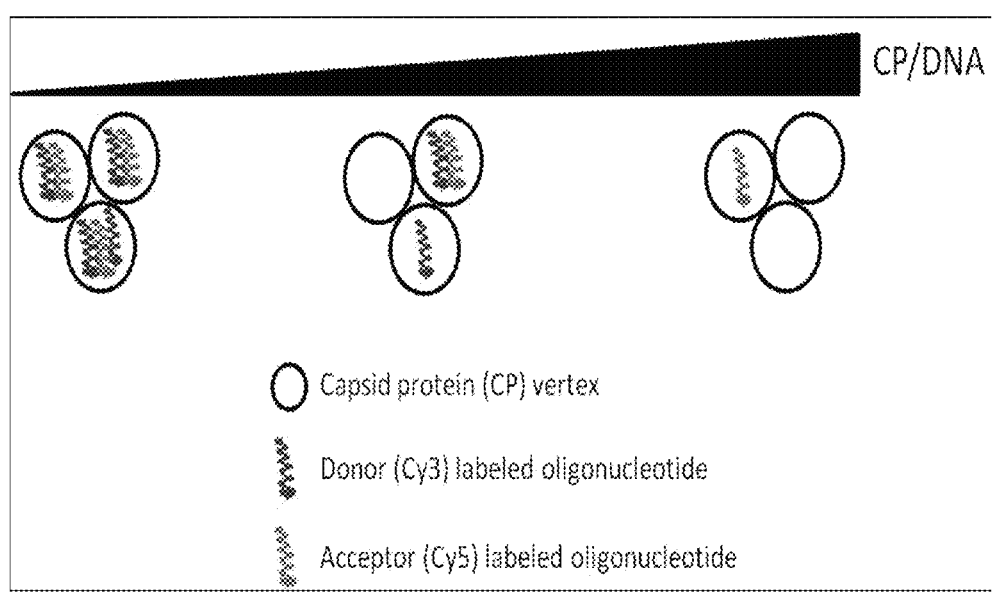
FIG. 3. Schematic of HBV Cp183 binding to nucleic acid showing effects of oligonucleotide dilution. Top panel ramp represents increasing amounts of capsid protein (CP) per ssDNA unit. This corresponds to a decrease in the number of oligonucleotides bound per vertex of protein. The result is an increase in FRET signal at low CP/DNA until some optimum maximum ratio, followed by a drop in FRET signal intensity.

The results for HBV show first a rapid increase in signal to a maximum intensity, similar to that of BMV, at three proteins per core protein monomer. This is then followed by a decrease in signal intensity. The strong FRET response suggests that HBV Cp183, like BMV capsid protein, binds multiple nucleic acids per vertex. However, as Cp183 dimer concentration increases beyond the signal maximum less oligonucleotides are bound per vertex. This dilution effect results in the observed diminishing intermolecular energy transfer until eventually less than one oligonucleotide is bound per vertex (FIG. 3). In contrast, HIV-1 shows minimal FRET signal changes with the 27-mer even though electron micrographs confirm that GagΔ does bind nucleic acid and assembles into capsids and nucleoprotein complexes (FIG. 1D inset).

Example 2. Intramolecular FRET

GagΔ does not induce FRET from separate D and A oligomers, though the oligomers induce assembly of complexes that scatter light and are capsid-like in electron micrographs. This is consistent with binding of only one oligonucleotide per cluster of GagΔ molecules, a hexagonal vertex of GagΔ. To use fluorescence to assay GagΔassembly, DNA induced bending of a double-labeled oligonucleotide upon protein interaction results in observable FRET signal. An assay system was used based on a 40-mer was labeled at both ends with D and A (referred to as DA).

Figure 4:
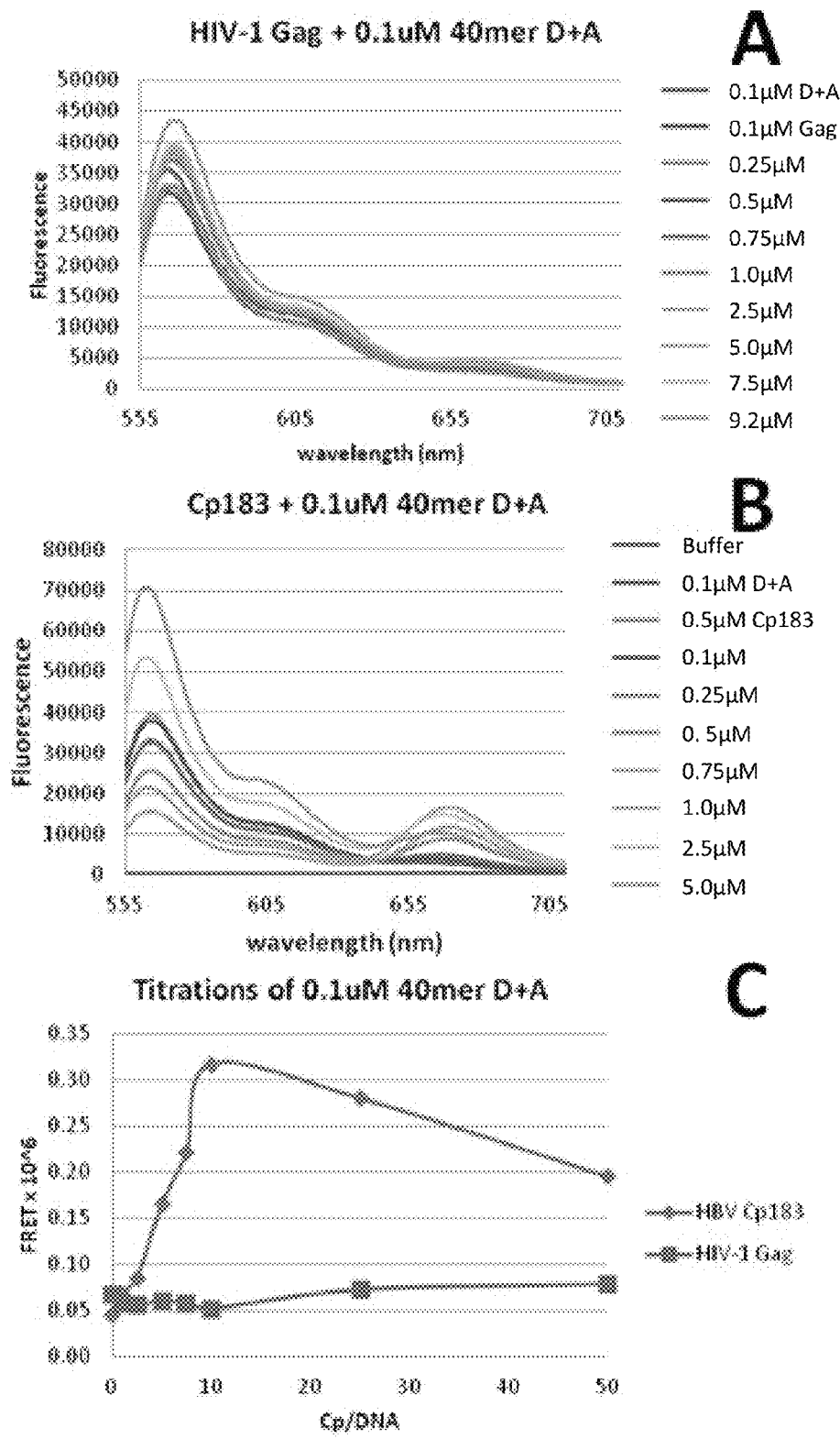
FIG. 4. Emission spectra from assembly reactions of HIV-1 GagΔ and HBV Cp183 to individually labeled 40-mer (A) and (B) respectively, and double-labeled 40-mer (E) and (F) respectively. All titrations were carried out with 0.1 µM 40-mer. Changes in FRET signal intensity (C) and (G) and normalized results of acceptor/donor emission maxima (D) and (H) are compared for both viruses.

In this example, FIG. 4 shows reactions conducted by titrating 0.1 µM DA with GagΔ. The advantage of using a fluorescence-based method is its sensitivity allows us to work at concentrations lower than what has previously been reported in the literature (Fisher, 1998; Campbell and Rein, 1999; Datta and Rein, 2009; Porterfield et al., 2010). DA by itself had minimal FRET signal but as shown, this was enhanced more than two-fold upon protein binding. The excess FRET signal observed here was thus due solely to intramolecular energy transfer upon protein-induced bending of the oligonucleotide.

For comparison, DA was titrated with Cp183 and the results were compared to those obtained with GagΔ. FIGS. 4A and 4B show the spectra for HIV-1 GagΔ and HBV Cp183 respectively. Spectra obtained by titrating DA with GagΔ and Cp183 both show increases in FRET signal.

Normalized titration results show that the signal from HIV levels off at approximately 6:1 protein-DNA ratio, suggesting that GagΔ hexamer formation drives assembly (FIG. 4D). This confirms nucleic acid binding with HBV is primarily a result of intermolecular interactions and that HBV assembly is dominated more by protein-protein interactions than by protein-nucleic acid ones.

Conclusions

We have successfully developed an in vitro FRET-based assembly assay and shown that it is generally applicable to at least four different classes of viruses. This two-model system is a platform for studying the nature of protein-nucleic acid binding under typical in vitro conditions. The assay is sensitive and can be used at nucleic acid concentrations as low as 50 nM. We observe two modes of DNA binding for virus assembly to short ssDNA oligonucleotides. In the first, capsid proteins bind oligonucleotides in clusters (presumably structural vertices) to promote protein-protein interactions allowing intermolecular FRET between D and A oligonucleotides as ssen with RRV, HBV and BMV. In the second mode, a single oligonucleotide is found at a cluster of subunits so that there is negligible D and A FRET but considerable intramolecular FRET from a DA oligonucleotide, as demonstrated with GagΔ. The binding mode of a given virus may suggest roles for protein-protein versus protein-nucleic acid interactions.

Example 3. Using Generalized FRET-Based Assembly Assay to Screen Small Molecules that Acts on Virus Assembly Assembly-directed antivirals may work by blocking assembly or by inappropriately activating assembly. Either strategy is antiviral, though enhancing assembly seems counter-intuitive. Since assembling a virus requires careful timing of events (like an assembly line), activating assembly at the wrong time can lead to defective or empty virus-like particles. By consuming hundreds of proteins at the cost of a few "assembly enhancers" one can leverage the utility of the antiviral.

In this example we further use above generalized FRET based assembly assay to screen small molecules that can act on virus assembly. The assembly conditions in these screening assays may be different from physiological conditions. In order to assay for molecules that enhance assembly, we need to have conditions where assembly without drug does not go to 100%. To identify inhibitors of assembly we need conditions where association is not very strong compared to the effect of the molecule. For this reason, the assembly conditions must be chosen so that assembly only goes to 25-50%. This level of assembly gives dynamic range to the assay, making it possible to see enhancing or inhibiting effect.

Taking HIV Gag assembly as an example, we introduce "mutant Gag" as the capsid protein, because there are many mutants that are easier to work with in the assembly solution, at the same time they have very similar assembly activity.

Briefly, a fluorophore labeled oligonucleotide DA is synthesized according to the "materials and methods" to study HIV Gag protein-nucleotide assembly. HIV Gag capsid protein, or a mutant form of Gag (e.g. GagΔ), at titrated concentration is added to assemble fluorophore labeled DA. According to the result in Example 2, the assembly is to be in a manner of several Gag capsid proteins binding to one oligonucleotide and the FRET signal is observed in the absence of any testing molecule.

To attenuate the association of the Gag or Gag mutant protein for the labeled nucleotide, the solution condition of the assembly is varied by modulating electrostatic protein-nucleic acid interactions, for example, by adjusting ionic strength—high salt will weaken binding and thus assembly. Another approach to attenuate the association of Gag or Gag mutant protein for the labeled nucleotide is to modulate protein-protein interactions. Many such interactions are sensitive to pH or chaotropes (e.g. guanidinium HCl or urea). Yet another approach is to use a shorter or longer oligonucleotide to improve or attenuate interaction with nucleic acids or between subunits.

With an attenuated association of the GagΔ for the nucleotide, we then add a testing molecule to the labeled DA and capsid protein mixture. If the testing molecule reduces or enhances FRET signal compared to the control, it is identified as an assembly target molecule to disable viral assembly or produce disabled or empty viral particle, depriving all the capsid proteins without packing correct viral genome.

It should be understood that the foregoing relates to exemplary embodiments of the disclosure and that modifications may be made without departing from the spirit and scope of the invention as set forth in the following claims.

The invention claimed is:

1. A generalized in vitro viral assembly assay system, comprising:
   a. a concentration of at least one generalized oligonucleotide that is fluorophore labeled, wherein said fluorophore is either a donor (D), an acceptor (A), or both (DA), wherein (a) length of said generalized oligonucleotide, (b) sequence of said generalized oligonucleotide, and (c) D and A ratio are optimized to obtain energy transfer from D to A; and
   b. a concentration of unlabeled viral capsid protein titrated relative to the concentration of said fluorophore labeled generalized oligonucleotide, wherein said unlabeled viral capsid protein assembles so that said fluorophore labeled generalized oligonucleotide is associated with the resulting viral nucleocapsid particles and generates a D to A fluorescent signal.

2. The assay system according to claim 1, wherein D is a fluorescence energy resonance transfer (FRET) donor, A is a FRET acceptor, and the fluorescent signal is a FRET signal.

3. The assay system according to claim 1, further comprising unlabeled generalized oligonucleotides to prevent self-quenching.

4. The assay system according to claim 1, wherein said unlabeled viral capsid protein is from a self-assembling virus, and said unlabeled viral capsid protein contains a DNA or RNA binding motif.

5. The assay system according to claim 4, wherein said self-assembling virus is selected from:
   togaviridae, flaviviridae, hepadnaviridae, astroviridae, birnaviridae, bunyaviridae, caliciviridae, coronaviridae, Deltaviridae (HDV), papillomaviridae, paramyxoviridae, polyomaviridae, retroviridae, bromoviridae, caulimoviridae, dianthoviridae, sobemoviridae, tombusviridae, and tymoviridae.

6. The assay system according to claim 1, wherein said unlabeled viral capsid protein is from a virus selected from Hepatitis B Virus (HBV), Ross River Virus (RRV), Brome Mosaic Virus (BMV), and Human Immunodeficiency Virus (HIV).

7. The assay system according to claim 1, wherein said fluorophore labeled generalized oligonucleotide comprises between about 5 and about 50 nucleotides.

8. The assay system according to claim 1, wherein said fluorophore labeled generalized oligonucleotide D or A has no self-complementary sequence.

9. The assay system according to claim 1, wherein said fluorophore labeled generalized oligonucleotide DA comprises a string of 15 to 40 consecutive adenosines.

10. The assay system according to claim 1, wherein said fluorophore labeled generalized oligonucleotide is 5'-TGT GTG TGT GAA AAA AAA AAA AAA AAA AAA TGT GTG TGT G-3' (SEQ ID NO: 1) or 5'-TAC CCA CGC TCT CGC AGT CAT AAT TCG-3' (SEQ ID NO: 2).

11. The assay system according to claim 2, wherein said FRET signal is indicative of capsid assembly.

12. The assay system according to claim 11, wherein said unlabeled viral capsid protein forms a complex that interacts with multiple strands of said fluorophore labeled generalized oligonucleotide, wherein said viral capsid assembly:
   a. maximizes the number of labeled nucleotides per capsid, area or unit length; and
   b. maximizes intermolecular FRET.

13. The assay system according to claim 11, wherein said viral capsid assembly:
   a. restricts a number of fluorophore labeled generalized oligonucleotides per capsid, area, or unit length;
   b. minimizes intermolecular FRET; and
   c. supports intramolecular FRET;
wherein a doubly-labeled DA generalized oligonucleotide optionally is used.

14. A method to screen molecules that target viral assembly, comprising:
   a. providing a generalized viral assembly assay system that includes:
      (i) a chemically relevant concentration of at least one generalized oligonucleotide that is fluorophore labeled, wherein said fluorophore is either a donor (D), an acceptor (A), or both (DA), wherein a ratio of D and A is optimized to obtain energy transfer from D to A; and
      (ii) a titrated concentration of viral capsid protein, wherein said viral capsid protein and said fluorophore labeled generalized oligonucleotide partially assemble into a labile complex;
   b. applying a testing molecule to said viral assembly assay system; and
   c. measuring a fluorescent signal to ascertain the effect of said testing molecule on viral assembly.

15. A method to screen molecules that target alphavirus capsid assembly, comprising:
   a. providing a first fluorophore labeled generalized oligonucleotide, wherein said fluorophore is a donor (D), a second fluorophore labeled generalized oligonucleotide, wherein said second fluorophore is an acceptor (A), and excess unlabeled generalized oligonucleotide;
   b. providing an alphavirus capsid protein or a mutant capsid protein at titrated concentration sufficient to allow said capsid protein to assemble on many generalized oligonucleotides to produce maximum fluorescent signal;
   c. altering solution conditions to attenuate the association of the capsid protein or the mutant for the nucleotide and produce a reduced fluorescent signal; and
   d. providing a testing molecule to said labeled generalized oligonucleotide capsid protein mixture, wherein said molecule reduces or enhances fluorescent signal compared to step c.

16. The method according to claim 14, wherein D is a fluorescence energy resonance transfer (FRET) donor, A is a FRET acceptor, and the fluorescent signal is a FRET signal.

17. The method according to claim 14, wherein said testing molecule is an antiviral agent that may either promote or inhibit capsid assembly.

18. The method according to claim 14, wherein said solution conditions provide a dynamic range to said testing molecules that may enhance said capsid protein or said mutant capsid protein assembly.

19. The method according to claim 14, wherein said viral capsid protein is from HIV and said testing molecule affects the ability of HIV Gag to assemble in the presence of said DA.

20. A method to screen molecules that target HIV Gag assembly, comprising:
   a. providing a fluorophore labeled oligonucleotide DA, wherein said DA has consecutive adenosines;
   b. providing an HIV Gag protein, or a mutant form of Gag protein, at titrated concentration so that an HIV Gag capsid protein or an HIV Gag mutant capsid protein assembles with said fluorophore labeled oligonucleotide DA in a manner of several capsid proteins binding to one oligonucleotide to give maximum fluorescent signal;
   c. contriving solution conditions to attenuate the association of the Gag protein or the mutant Gag for the nucleotide and produce a reduced fluorescent signal; and
   d. providing a testing molecule to said fluorophore labeled oligonucleotide DA and Gag protein mixture, wherein said molecule reduces or enhances fluorescent signal compared to step c.

21. The method according to claim 20, wherein the fluorescent signal is a FRET signal.

22. The method according to claim 20, wherein said solution conditions provide a dynamic range to said testing molecules that may enhance said Gag protein or said mutant Gag protein assembly.

23. The method according to claim 20, wherein said testing molecule affects the ability of HIV Gag to assemble in the presence of said fluorophore labeled oligonucleotide DA.

* * * * *